(12) United States Patent
Davis et al.

(10) Patent No.: US 11,020,579 B2
(45) Date of Patent: Jun. 1, 2021

(54) COMBINED ARTERIAL VENOUS FISTULA GRAFT IMPLANT AND METHOD OF USING SAME

(71) Applicant: Cook Medical Technologies LLC, Bloomington, IN (US)

(72) Inventors: Barrett Davis, West Lafayette, IN (US); Kalub Hahne, West Lafayette, IN (US)

(73) Assignee: Cook Medical Technologies: LLC, Bloomington, IN (US)

( * ) Notice: Subject to any disclaimer, the term of this patent is extended or adjusted under 35 U.S.C. 154(b) by 559 days.

(21) Appl. No.: 16/013,148

(22) Filed: Jun. 20, 2018

(65) Prior Publication Data

US 2018/0369554 A1 Dec. 27, 2018

Related U.S. Application Data

(60) Provisional application No. 62/522,922, filed on Jun. 21, 2017.

(51) Int. Cl.
*A61M 39/02* (2006.01)
*A61F 2/06* (2013.01)
*A61M 1/36* (2006.01)

(52) U.S. Cl.
CPC .......... *A61M 39/0247* (2013.01); *A61F 2/06* (2013.01); *A61F 2/064* (2013.01); *A61M 1/3655* (2013.01); *A61F 2002/065* (2013.01); *A61F 2002/067* (2013.01); *A61F 2230/0054* (2013.01); *A61F 2250/0039* (2013.01); *A61M 2039/027* (2013.01); *A61M 2039/0258* (2013.01); *A61M 2039/0261* (2013.01); *A61M 2039/0276* (2013.01); *A61M 2039/0282* (2013.01)

(58) Field of Classification Search
CPC ............ A61M 39/0247; A61M 1/3655; A61M 2039/0258; A61M 2039/0261; A61M 2039/027; A61M 2039/0276; A61M 2039/0282; A61F 2/06; A61F 2/064; A61F 2002/065; A61F 2002/067; A61F 2230/0054; A61F 2250/0039
See application file for complete search history.

(56) References Cited

U.S. PATENT DOCUMENTS

| | | | |
|---|---|---|---|
| 4,822,341 A | 4/1989 | Colone | |
| 8,366,651 B2 * | 2/2013 | Dakin | A61M 27/002 604/8 |
| 9,174,037 B2 | 11/2015 | Schutz et al. | |

(Continued)

FOREIGN PATENT DOCUMENTS

WO 2010028272 3/2010

*Primary Examiner* — Philip R Wiest
(74) *Attorney, Agent, or Firm* — Liell & McNeil

(57) ABSTRACT

A patient may be treated by implanting a combined arterial venous fistula graft implant in a limb of the patient. The combined implant includes a body with a vessel segment in contact with an artery and a first tubular segment for attachment to an end of a vein to form an arterial venous fistula, and a second tubular segment with an attached segment of artificial tubing for attachment to the vein at a second location to form an arterial venous graft. The arterial venous graft may be exclusively used to form hemodialysis for a period of time after the implanting step, while the arterial venous fistula matures.

20 Claims, 4 Drawing Sheets

(56) References Cited

U.S. PATENT DOCUMENTS

| | | | |
|---|---|---|---|
| 2003/0083678 A1* | 5/2003 | Herweck | A61M 1/3661 606/153 |
| 2005/0154444 A1 | 7/2005 | Quadri | |
| 2010/1300995 | 5/2010 | Yevzlin et al. | |
| 2010/0268316 A1 | 10/2010 | Brenneman et al. | |
| 2014/0276327 A1* | 9/2014 | Deur | A61M 39/0208 604/6.16 |
| 2015/0257760 A1 | 9/2015 | Shields et al. | |

* cited by examiner

COMBINED ARTERIAL VENOUS FISTULA GRAFT IMPLANT AND METHOD OF USING SAME

TECHNICAL FIELD

The present disclosure relates generally to arterial venous fistulas and arterial venous grafts, and more particularly to a combined implant for simultaneously creating both an arterial venous fistula (AVF) and an arterial venous graft (AVG).

BACKGROUND

Maintaining vascular access during hemodialysis is a difficult task, confounded by multiple potential pitfalls with the current, readily available methodologies. Among these methodologies are arterial venous fistulas, arterial venous grafts and central venous catheterization. Some of the pitfalls include infection, stenosis, clotting, thrombosis and, in the case of an AVF, premature use. Despite the immediate need for venous access to treat end stage renal disease or chronic kidney disease, often premature AVF use damages a patient's natural vasculature beyond further usage, significantly impairing future venous access.

In some rare instances, a surgeon will create an AVF in the same procedure as an AVG is implanted to provide an immediate vascular access point via the AVG. In this way, the AVG generally will not cause long term vascular damage from use, nor carry the particularly high risk of infection that central venous catheterizations do, while the AVF matures. Although this method can result in better patient outcomes, AVG's are prone to occlusion and eventually often become unusable, sometimes before the patient's newly created AVF has sufficiently matured for proper usage. In other words, the AVG may become occluded beyond use before an AVF becomes sufficiently mature for proper vascular access.

The present disclosure is directed toward one or more of the problems set forth above.

SUMMARY OF THE DISCLOSURE

In one aspect, a combined arterial venous fistula graft implant includes a body with a vessel segment having a length and an arched width to match an artery shape and define an artery centerline. The body includes a first tubular segment and a second tubular segment that extend away from the vessel segment. The first tubular segment terminates at an AVF port, and the second tubular segment terminates at an AVG port. The body defines an AVF passage that opens at one end through the vessel segment and at an opposite end through the AVF port. An AVG passage opens at one end through the vessel segment and at an opposite end through the AVG port. Exactly one segment of artificial tubing is attached to the body, and the artificial tubing is attached to the second tubular segment at the AVG port. The artificial tubing has a lumen fluidly connected to the AVG passage.

In another aspect, a method of treating a patient includes implanting a combined arterial venous fistula graft implant in a limb of the patient. The implanting step includes fluidly connecting an artery to a first location of a vein via an AVF passage of the implant and to a second location of the vein via an AVG passage of the implant. An arterial venous graft, which includes the AVG passage, is used exclusively to perform hemodialysis for a period of time after the implanting step while an arterial venous fistula, which includes the AVF passage matures.

DETAILED DESCRIPTION

Figure 1:
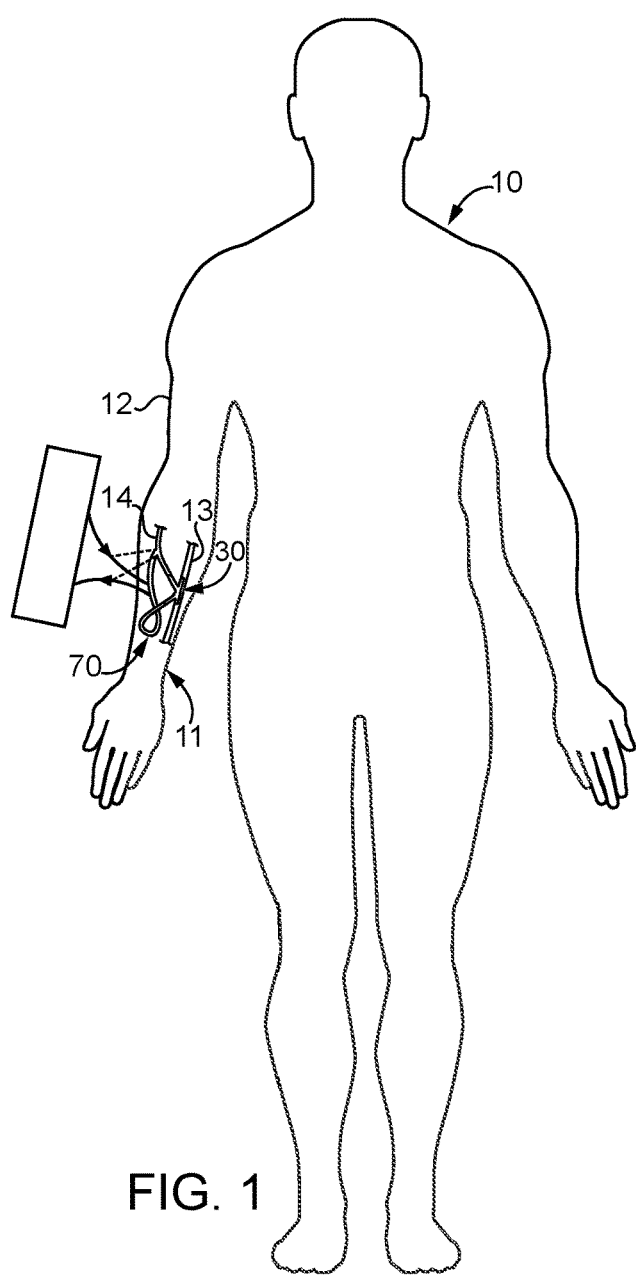
FIG. 1 is a schematic view of a patient undergoing hemodialysis.

Referring initially to FIGS. 5-10, a combined arterial venous fistula graft implant 30 includes a body 31 and exactly one segment of artificial tubing 70 attached thereto. The body 31 includes a vessel segment 32 with a length 40 and an arched width 41 to match an artery shape and define an artery centerline 20. The body 31 includes a first tubular segment 33 and a second tubular segment 34 that both extend away from the vessel segment 32. The first tubular segment 33 terminates at an AVF port 42, while the second tubular segment 34 terminates at an AVG port 43. The body 31 defines an AVF passage 35 that opens at one end 44 through the vessel segment 32 and at an opposite end 45 through the AVF port. An AVG passage 36 opens at one end 46 through the vessel segment 32 and at an opposite end 47 through the AVG port 43. The artificial tubing 70, which may have a length maybe on the order of 60 centimeters has a first end 73 attached to the second tubular segment 34 at the AVG port 43. The artificial tubing 70 has a lumen 71 fluidly connected to the AVG passage 36. Although not necessary, the body 31 maybe made in an integral uni-body design out of a suitable biocompatible thermoplastic or maybe titanium, or any other suitable material known in the art. Although body 31 in the illustrated embodiment has an integral uni-body construction, it may be made from two or more component parts that are attached to one another in a manner well known in the art, which may or may not be of the same material. The biocompatible thermoplastic could be polyurethane or any other suitable thermoplastic. The artificial tubing 70, can be constructed of any suitable biocompatible material, such as, for instance, PTFE. In all instances, body 31 will be more rigid than the connected flexible artificial tubing 70.

The vessel segment 32 of the body 31 has an upstream end 48, in relation to arterial flow, and a downstream end 49. Although not necessary, the AVF port 42 may be closer to the upstream end 48 than the downstream end 49, but other configurations would also fall within the intended scope of the present disclosure. The first tubular segment 33 may define an AVF centerline 50 that is oriented at an angle 54 between 20°-40°, preferably 30°, with respect to the artery centerline 20. The angle 54 is best determined where the AVF passage 36 fluidly connects to the artery. In the illustrated embodiment, the AVF centerline 50 is straight, but curved configurations could also fall within the intended scope of the present disclosure. In the illustrated embodiment, the AVF passage 35 opens through the vessel segment 32 at a first opening 51. The AVG passage 36 opens through the vessel segment 32 at a second opening 52 that is spaced away from the first opening 51 by a separation distance 69 along the artery centerline 20. Nevertheless, the present disclosure contemplates structures in which the AVF passage and the AVG passage share a common segment such that they both open into or through vessel segment 32 at a shared opening. In addition, the present disclosure contemplates structures in which the relative positioning of the first opening 51 and the second opening 52 are reversed relative to the embodiment illustrated in FIGS. 5-10.

Figure 5:
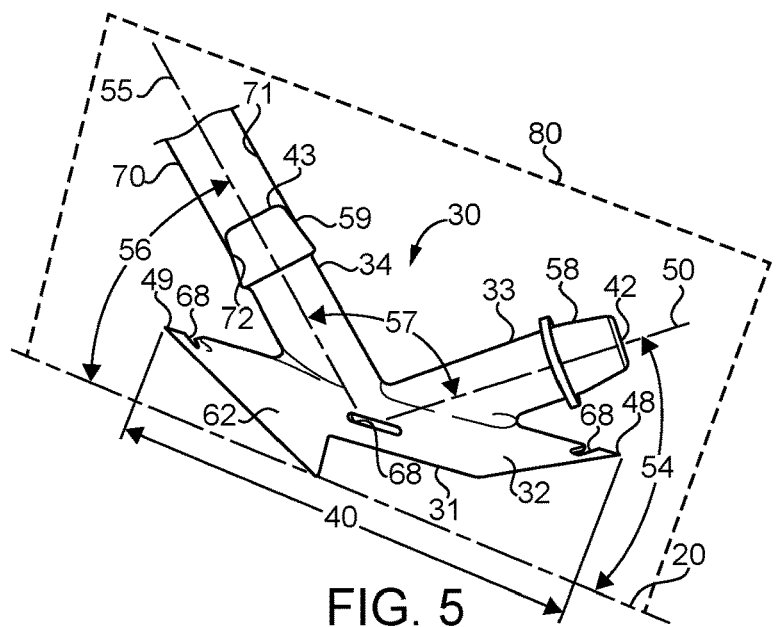
FIG. 5 is a side view of the combined implant according to the present disclosure.
Figure 6:
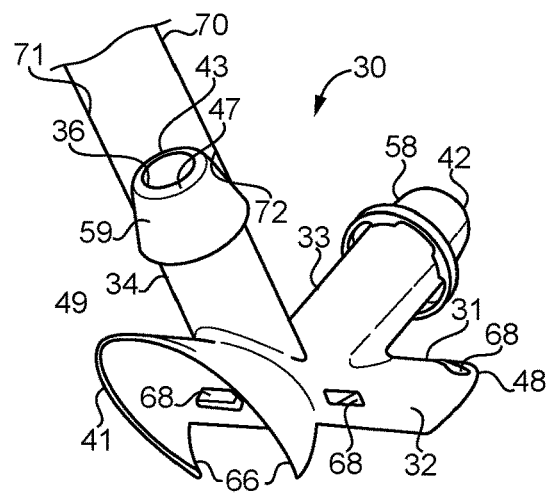
FIG. 6 is a front perspective view of the implant of FIG. 5.
Figure 7:
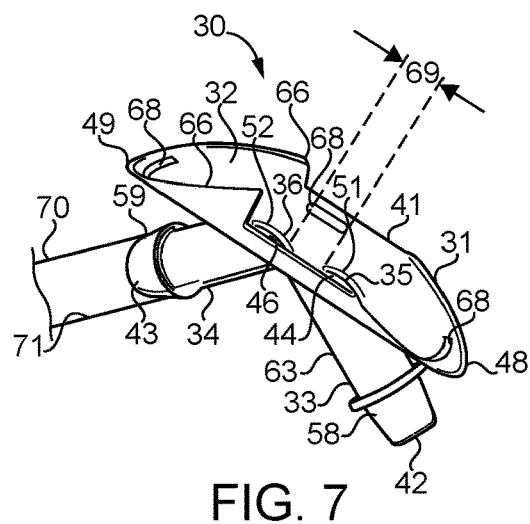
FIG. 7 is an underside perspective view of the implant of FIG. 5.
Figure 8:
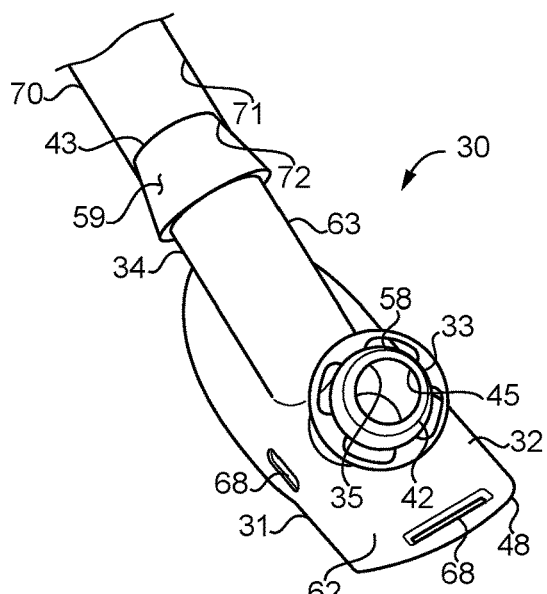
FIG. 8 is a front/top perspective view of the implant of FIG. 5.
Figure 9:
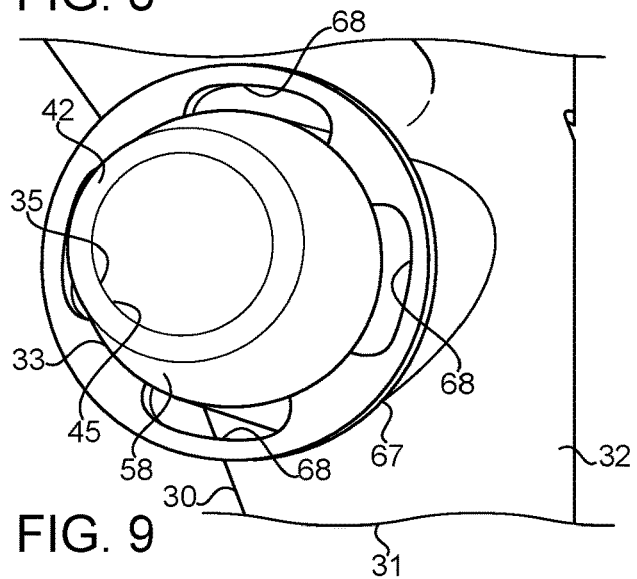
FIG. 9 is an enlarged perspective view of the AVF port region of the implant of FIG. 5.
Figure 10:
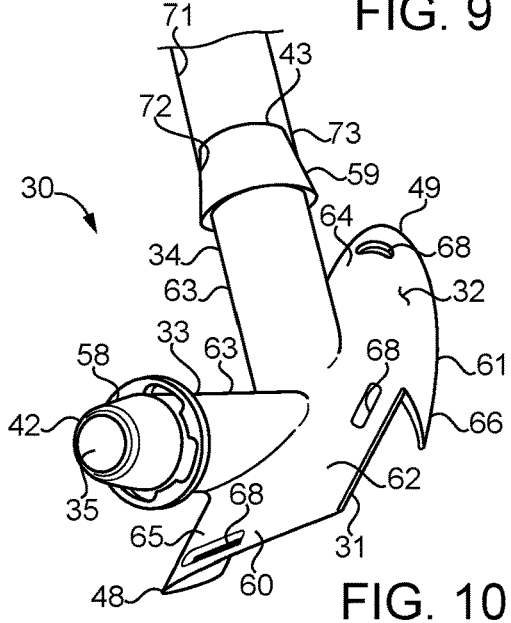
FIG. 10 is a top/front perspective view of the implant of FIG. 5.

The second tubular segment 34 may define an AVG centerline 55 that is oriented at an acute angle 56 with respect to the artery centerline 20, but oriented at an obtuse angle 57 with respect to the AVF centerline 50, as best shown in FIG. 5. Nevertheless, acute angle 56 could be a right angle or an obtuse angle and/or the obtuse angle 57 could be a right angle or an acute angle without departing from the present disclosure. In the illustrated embodiment, the body 31 defines exactly one plane of symmetry 80 so that the implant 30 can be equally suited for implantation in either a left arm or a right arm of a patient. The plane of symmetry 80 may contain the artery centerline 20, the AVF centerline 50 and the AVG centerline 55. Nevertheless, those skilled in the art will appreciate that an implant according to the present disclosure could have no plane of symmetry or two or more planes of symmetry without departing from the present disclosure.

In one aspect, the AVF port 42 may have an external venous attachment surface 58 that can come in various shapes according to strategies well known in the art. In one example case, as per the illustrated embodiment, the external venous attachment surface 58 may include a collar 67 with a plurality of suture windows 68 to help facilitate attachment of a venous end to the AVF port 42. The AVG port 43 also may have an external attachment surface 59 that is in contact with an internal surface 72 of the artificial tubing 70, and have a shape different from the external venous attachment surface 58. Nevertheless, those skilled in the art will appreciate that the AVF port and the AVG port may have identical shapes, or the AVG port may be configured to contact an external surface of the artificial tubing 70 so that the tubing is received within the port, without departing from the present disclosure. Thus, the shapes and attachment strategies for the AVF port 42 and the AVG port are a matter of design choice and may be identical or different without departing from the present disclosure.

Figure 3:
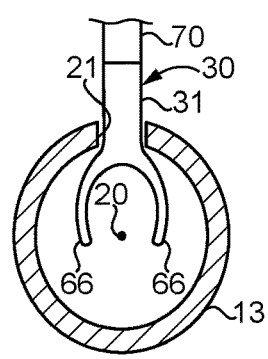
FIG. 3 is a sectioned view through an artery while the combined implant of the present disclosure is being connected to an artery.

The vessel segment 32 of body 31 may have a first shape 60 at upstream end 48 and a different shape 61 at the opposite or downstream end 49. Nevertheless, those skilled in the art will appreciate that the vessel segment could have identically shaped ends without departing from the present disclosure. In addition, the implant 30 of the illustrated embodiment includes the body 31 having an intravascular portion 62 that includes the vessel segment 32 for positioning within an artery, and an extravascular portion 63 that includes both the first tubular segment 33 and the second tubular segment 34. Nevertheless, those skilled in the art will appreciate that the body 31 could be entirely extravascular such that the vessel segment attached to, and came in contact with, an external surface of an artery rather than an internal arterial wall surface 22 as in illustrated embodiment. In addition, although not necessary, the vessel segment 32 is shown as including a plurality of suture windows 68 to better facilitate attachment of body 31 to an artery during implantation. The body may include from zero to many suture windows without departing from the present disclosure. In the illustrated embodiment, the downstream end 49 of vessel segment 32 has a first surface area 64, and the upstream end 48 has a different surface area 65. In the illustrated embodiment, and in reference to additional FIGS. 3 and 4, the first surface area 64 at downstream end 49 may include a pair of deformable wings 66 that resiliently deform away from the match with the artery shape toward the artery centerline 20 (FIG. 3) for passage through an artery opening 21. After passage through the artery opening 21, the deformable wings 66 may resiliently deform back to match the artery shape to be in contact with arterial wall 22 after being positioned within the artery 13.

Figure 11:
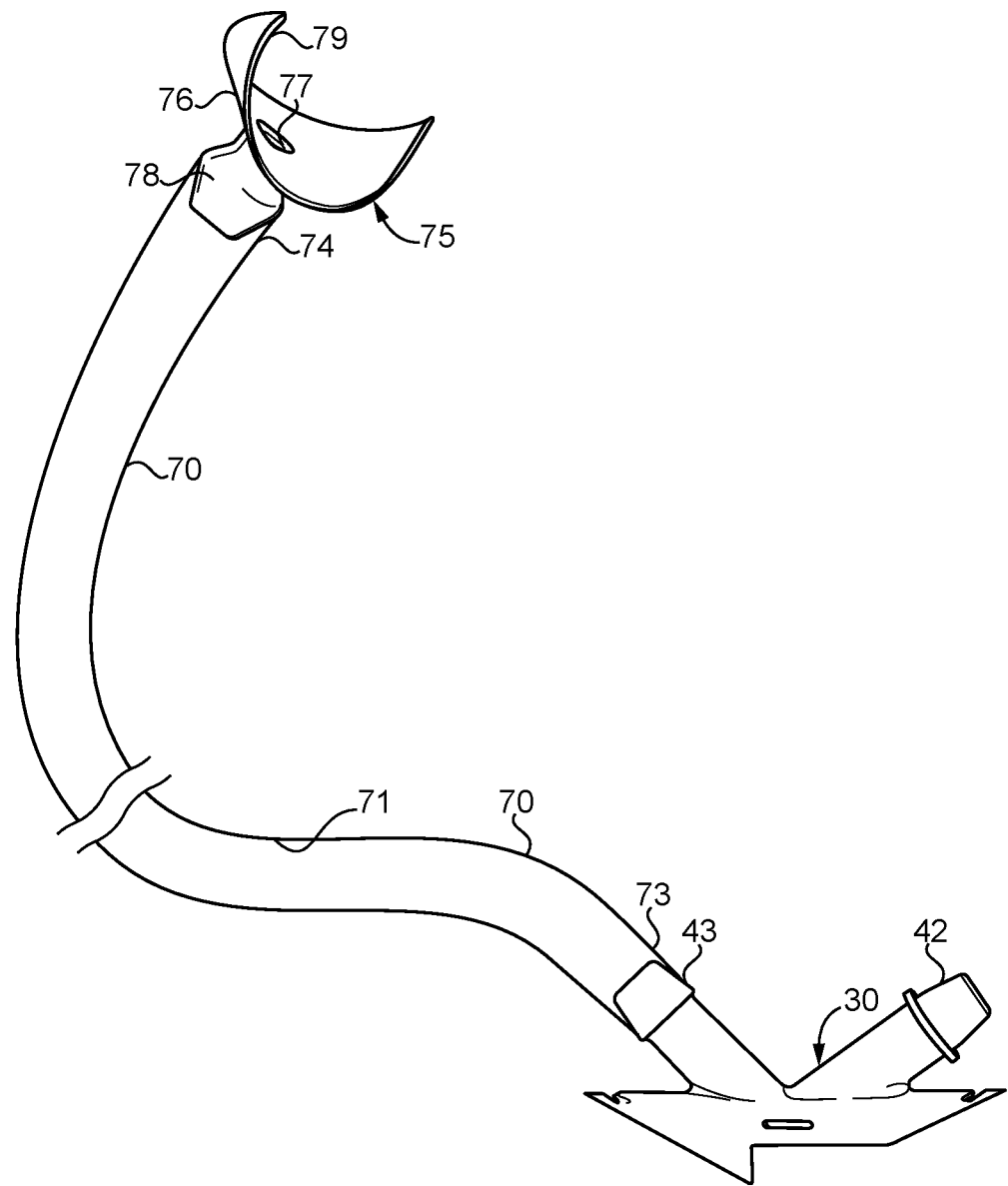
FIG. 11 is a schematic view of a combined three-part implant according to the present disclosure.

In the embodiment of FIGS. 5-10, the combined arterial fistula graft implant 30 may be such that the remote end 74 of artificial tubing 70 is configured for direct attachment to a vein. Or, as illustrated in the embodiment of FIG. 11, a separate venous connector 75 may be attached to remote tubing end 74 so that the artificial tubing 70 is fluidly connected to the vein via the venous connector 75. The venous connector 75 may be of a unibody design and constructed of the same material as the body 31 of the combined arterial venous fistula grafted implant 30, and include a body 76 that includes an arched segment 79 and a vein port 78. The body 76 defines an opening 77 that fluidly connects to the internal lumen 71 of artificial tubing 70. The arched segment 79 may be configured to be positioned within the attached vein and be flexible so that the arched segment 79 is urged into contact with the inner wall of the vein, even as the vein enlarges after the initial implantation procedure. Thus, the venous connector 75 may include an intravenous portion (arched segment 79) and an extravenous portion that includes the vein port 78.

The embodiment of FIGS. 5-10 show an embodiment that includes two parts, namely the combined implant 30 and the artificial tubing 70 whereas the embodiment of FIG. 11 includes three parts with the inclusion of the venous connector 75. Nevertheless, those skilled in the art will appreciate that other embodiments with more than three parts could also fall within the intended scope of the present disclosure.

INDUSTRIAL APPLICABILITY

The present disclosure finds general applicability for any patient needing venous access, such as for hemodialysis. The present disclosure finds particular applicability for those patients who could benefit from initially gaining venous access via an arterial venous graft, and then later venous access via an arterial venous fistula, after maturation.

Figure 2:
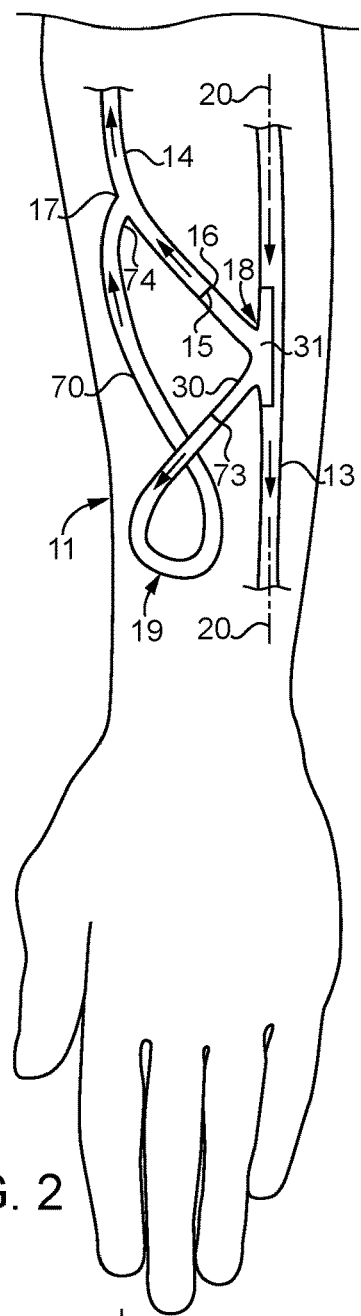
FIG. 2 is an enlarged schematic view of an arm of the patient from FIG. 1.
Figure 4:
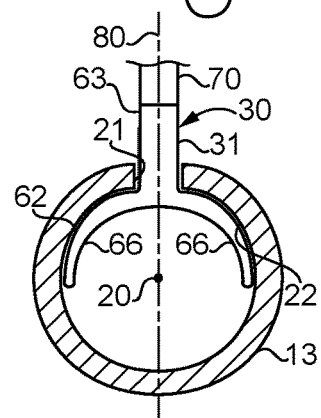
FIG. 4 is a cross sectional view similar to that of FIG. 3 after the deformable wings of the implant have resiliently moved into contact with the arterial wall during an implantation procedure.

Referring now in addition to FIGS. 1 and 2, a method of using a combined arterial fistula graft implant 30 includes securing the vessel segment 32 to an artery 13. In the illustrated embodiment, this may be accomplished using the suture windows 68 and appropriate sutures. Nevertheless, other attachment strategies could be utilized. For instance, to securely fix an extravascular version of vessel segment 32, a surgeon might use a vessel compatible adhesive glue and/or suture points included along the edges of the device. Although asymmetrical hooking mechanism type shapes might help keep the device from moving during placement, the compliant and pulsatile nature of the arterial vasculature would likely prohibit only this type of hooking mechanism from forming a strong fixture with an inlet artery without a secondary means of attachment, such as suturing. When the vessel segment 32 is for intravascular placement, as in the illustrated embodiment, the device could benefit from the outward radial pressure force of blood flow through the artery to keep the device fixed in place and reduce leakage. These particular adaptations might also benefit from a slight oversizing of the deformable wings 66 so that the deformable wings could span to tightly press fit into the artery 13 interior diameter. This may be important, as in addition to any sutures running from an exterior of the artery 13 to the interior of the device and back out, a press-fit coincident between the implant 30 and the artery 13 could act to turn the arterial wall 22 into a sort of o-ring seal around the implant's profile. After the vessel segment 32 is secured to the artery 13, an arterial venous fistula 18 is created by attaching an end 15 of a vein 14 to the AVF port 42. An arterial venous graft 19 is then created by fluidly connecting the remote end 74 of the artificial tubing 70 to the vein 14. In the illustrated embodiment, the vessel segment 32 is positioned within artery 13, as shown in FIG. 4. Also, the illustrated embodiment shows the implant 30 located in an arm 12 of patient 10. However, those skilled in the art will appreciate that other locations in the patients body could work equally well, and also fall within the present disclosure.

From another perspective, a method of treating a patient 10, which may be live or artificial, includes implanting the combined arterial venous fistula graft implant 30 in a limb 11 of the patient 10. The implanting step includes fluidly connecting the artery 13 to a first location 16 of vein 14 via the AVF passage 35 of the implant 30 and to a second location 17 of the vein 14 via the AVG passage 36 of the implant 30. In some instances, the arterial venous graft 19, which includes the AVG passage 36, may be exclusively used to perform hemodialysis for a period of time after the implantation step while the arterial venous fistula 18, which includes the AVF passage 35 matures until being ready for usage. In some cases, the arterial venous fistula 18 may be exclusively used to perform hemodialysis after the period of time associated with the arterial venous graft. For instance, usage of the arterial venous fistula may be initiated after the arterial venous graft 19 becomes partially or wholly occluded.

With reference again to the embodiment illustrated in FIGS. 5-10 and FIG. 11, the uni-body design may include the vessel segment 32 having an arched width defining a diameter in a range of 0.75 to 1.25 millimeters and a length 40 in a range of 5-20 millimeters. In addition, the openings 51 and 52 through the vessel segment 32 may have an ellipsoid shape, maybe with minor diameters in the range of 2-4 millimeters. The internal diameters of the AVF passage 35 and the AVG passage 36 may be identical or maybe different but may likely be in a range of about 1.5 to 2 millimeters. The AVF port 43 may be sized for attachment to venous structures in a range of 2-4 millimeters in internal diameter. Although these dimensions may be suitable for one exampled embodiment, those skilled in the art will appreciate that these suggested dimensions are in no way limiting, and an implant according to the present disclosure could vary widely from these suggested dimensions without departing from the present disclosure.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A combined arteriovenous fistula graft implant comprising:
   a body that includes a vessel segment with a length and an arched width to match an artery shape and defining an artery centerline;
   the body including a first tubular segment and a second tubular segment that extend away from the vessel segment;
   the first tubular segment terminating at an AVF port;
   the second tubular segment terminating at an AVG port;
   the body defining an AVF passage that opens at one end through the vessel segment and at an opposite end through the AVF port, and an AVG passage that opens at one end through the vessel segment and at an opposite end through the AVG port; and
   exactly one segment of artificial tubing attached to the body, and the artificial tubing being attached to the second tubular segment at the AVG port, and having a lumen fluidly connected to the AVG passage.

2. The implant of claim 1 wherein the vessel segment has an upstream end and a down stream end; and
   the AVF port is closer to the upstream end than the downstream end.

3. The implant of claim 2 wherein the first tubular segment defines an AVF centerline that is oriented at an angle between twenty and forty degrees with respect to the artery centerline.

4. The implant of claim 3 wherein the AVF passage opens through vessel segment at a first opening; and
   the AVG passage opens through the vessel segment at a second opening that is spaced away from the first opening along the artery centerline.

5. The implant of claim 3 wherein the second tubular segment defines an AVG centerline oriented at an acute angle with respect to the artery centerline and oriented at an obtuse angle with respect to the AVF centerline.

6. The implant of claim 1 wherein the AVF port has an external venous attachment surface;
   AVG port has an external attachment surface in contact with an internal surface of the artificial tubing and has shape different from the external venous attachment surface.

7. The implant of claim 1 wherein the vessel segment has a first shape at one end and a different shape at an opposite end.

8. The implant of claim 1 wherein the body defines exactly one plane of symmetry.

9. The implant of claim 1 wherein the body has an intravascular portion that includes the vessel segment, and an extravascular portion that includes the first tubular segment and the second tubular segment.

10. The implant of claim 9 wherein the vessel segment has a first surface area at one end and a different surface area at an opposite end.

11. The implant of claim 10 wherein the first surface area includes a pair of deformable wings that resiliently deform away from the match of the artery shape toward the artery centerline for passage through an artery opening and resiliently deform back to the match of the artery shape after being positioned in an artery.

12. The implant of claim 1 wherein the body defines exactly one plane of symmetry, and the body has an intravascular portion that includes the vessel segment, and an extravascular portion that includes the first tubular segment and the second tubular segment;
   the vessel segment has a first surface area at an upstream end and a second surface area at downstream end that is larger than the first surface area; and
   the AVF port is closer to the upstream end than the downstream end and has an external venous attachment surface; and
   AVG port has an external attachment surface in contact with an internal surface of the artificial tubing and has shape different from the external venous attachment surface.

13. A method of using a combined arteriovenous fistula graft implant that includes a body with a vessel segment with a length and an arched width to match an artery shape and defining an artery centerline; the body including a first tubular segment and a second tubular segment that extend away from the vessel segment; the first tubular segment terminating at an AVF port; the second tubular segment terminating at an AVG port; the body defining an AVF passage that opens at one end through the vessel segment and at an opposite end through the AVF port, and an AVG passage that opens at one end through the vessel segment and at an opposite end through the AVG port; and exactly one segment of artificial tubing attached to the body, and the artificial tubing being attached to the second tubular segment at the AVG port, and having a lumen fluidly connected to the AVG passage, and the method comprising the steps of:
   securing the vessel segment to an artery;
   creating an arteriovenous fistula by attaching an end of a vein to the AVF port; and
   creating an arteriovenous graft by fluidly connecting the artificial tubing to the vein.

14. The method of claim 13 wherein the securing step includes positioning the vessel segment within the artery.

15. The method of any of claim 14 wherein the artery and the implant are located in an arm.

16. A method of treating a patient comprising the steps of:
   implanting a combined arteriovenous fistula graft implant in a limb of the patient;
   the implanting step including fluidly connecting an artery to a first location of a vein via an AVF passage of the implant and to a second location of the vein via an AVG passage of the implant;
   exclusively using an arteriovenous graft, which includes the AVG passage, to perform hemodialysis for a period of time after the implanting step while an arteriovenous fistula, which includes the AVF passage, matures.

17. The method of claim 15 including exclusively using the arteriovenous fistula to perform hemodialysis after the period of time.

18. The method of claim 16 wherein the step of exclusively using the arteriovenous fistula is initiated after the arteriovenous graft becomes occluded.

19. The method of claim 15 wherein the implanting step includes positioning a vessel segment of the implant within the artery.

20. The method of claim 18 including exclusively using the arteriovenous fistula to perform hemodialysis after the period of time.

* * * * *